United States Patent [19]

Brieva et al.

[11] Patent Number: 5,066,485

[45] Date of Patent: Nov. 19, 1991

[54] COSMETIC COMPOSITIONS COMPRISING OIL-IN-WATER EMULSION CONTAINING PIGMENT

[75] Inventors: Hernando Brieva, Manalapan, N.J.; Natividad Jose, Jamaica; Marlene Tietjen, New York, both of N.Y.

[73] Assignee: Revlon, Inc., New York, N.Y.

[21] Appl. No.: 579,180

[22] Filed: Sep. 5, 1990

Related U.S. Application Data

[63] Continuation of Ser. No. 453,363, Dec. 19, 1989, abandoned, which is a continuation of Ser. No. 259,464, Oct. 17, 1988, abandoned, which is a continuation of Ser. No. 11,971, Feb. 6, 1987, abandoned.

[51] Int. Cl.$^5$ .............................................. A61K 7/021
[52] U.S. Cl. ........................................ 424/63; 424/69; 514/772; 514/938; 514/941
[58] Field of Search ............................ 424/63, 64, 69; 514/772, 938, 941

[56] References Cited

U.S. PATENT DOCUMENTS

| | | | |
|---|---|---|---|
| 4,122,029 | 10/1978 | Gee et al. | 252/309 |
| 4,268,499 | 5/1981 | Keil | 514/772 X |
| 4,311,695 | 1/1982 | Starch | 514/938 X |
| 4,421,769 | 12/1983 | Dixon et al. | 514/772 |
| 4,532,132 | 7/1985 | Keil | 514/772 |
| 4,552,910 | 11/1985 | Deubzer et al. | 524/43 |
| 4,578,266 | 3/1986 | Tietjen et al. | 424/63 |
| 4,675,179 | 6/1987 | Suzuki et al. | 424/67 |

FOREIGN PATENT DOCUMENTS

| | | |
|---|---|---|
| 152953 | 8/1985 | European Pat. Off. . |
| 218509 | 9/1986 | Japan . |
| 2064363 | 6/1981 | United Kingdom . |

OTHER PUBLICATIONS

Kirk–Othmer Encyclopedia of Chemical Technology, 3rd Ed., vol. 7, pp. 143, 146–148 (1979), John Wiley & Sons.
Dow Corning brochure, "Information About Cosmetic Ingredients", c. 1980.
Down Corning brochure, "Information About Volatile Silicone Fluids", c. 1982.
Kollmeier et al, "Organo–Polysiloxanes for Cosmetic Formulations", (source unkonwn at present).
Union Carbide product information brochure, "Volatile Silicone Fluids" and Additional Silwet TM Surface Active Copolymers, c. 1980.

*Primary Examiner*—Thurman K. Page
*Assistant Examiner*—Susan S. Rucker
*Attorney, Agent, or Firm*—Julie Blackburn

[57] ABSTRACT

Compositions comprising oil-in-water emulsions are disclosed comprising pigment coated with polysiloxane; a silicone phase; a water phase; and a polydiorganosiloxane-polyoxyalkylene copolymeric surfactant.

8 Claims, No Drawings

COSMETIC COMPOSITIONS COMPRISING OIL-IN-WATER EMULSION CONTAINING PIGMENT

This application is a continuation of application Ser. No. 453,363, filed on Dec. 18, 1989 now abandoned which is a continuation of U.S. Ser. No. 259,464 filed on Oct. 17, 1988 now abandoned which is a continuation of U.S. Ser. No. 011,971 filed Feb. 6, 1987 now abandoned.

The present invention relates to cosmetic compositions in general and more specifically to compositions of an oil-in-water emulsion containing other cosmetically desirable components and pigment.

BRIEF SUMMARY OF THE INVENTION

The present invention comprises a cosmetic composition which is an oil-in-water emulsion comprising (a) an oil phase which comprises (i) a coated pigment consisting essentially of finely divided particles of pigment (inorganic or organic) whose surfaces are chemically bonded to, and physically completely coated by, polysiloxane which coating renders the particles hydrophobic, and (ii) a silicone component selected from the group consisting of dimethyl polysiloxane having the formula $(CH_3)_3SiO(Si(CH_3)_2O)_d$—$Si(CH_3)_3$ wherein the degree of polymerization d is effective to give the fluid a viscosity of 0.65 to one million centistokes at 25° C.; cyclomethicone having a degree of polymerization of 3 to 6; organopolysiloxane having the formula $$X(CH_3)_2SiO-Y-Si(CH_3)_2X$$

wherein X is alkyl or alkoxy having 1 to 30 carbon atoms and Y is a chain of 1 to 100 repeating (Si-O) units containing 1 to 100 units of the formula $(Si(R_1)(R_2)O-)$ and 0 to 100 units of the formula $(Si(R_3)(R_4)O)$ wherein each of $R_1$, $R_2$, $R_3$ and $R_4$ can be alkyl containing 2 to 30 carbon atoms, phenyl, or phenyl connected to the Si atom by a vinyl group or an alkylene bridge 1 to 3 carbon atoms long; wherein each $R_1$ and $R_3$ can also be —$CH_3$, and each $R_1$ and $R_2$ can also be trimethylsiloxy; and mixtures thereof;

(b) an agueous phase;

(c) a surfactant which is a polydiorganosiloxane-polyoxyalkylene copolymer containing at least one polydiorganosiloxane segment consisting of $$R_bSiO_{(4-b)/2}$$

siloxane units wherein b has a value of from 0 to 3 inclusive, there being an average of approximately 2 R radicals per silicon in the copolymer, and R denotes a radical selected from the group consisting of methyl, ethyl, vinyl, phenyl and a divalent radical of 2-6 carbons bonding a polyoxyalkylene segment to the polydiorganosiloxane segment, at least 95 percent of all R radicals being methyl; and containing at least one polyoxyalkylene segment having an average molecular weight of less than 5000 and consisting of from 0 to 50 mol percent polyoxypropylene units and from 50 to 100 mol percent polyoxyethylene units, at least one terminal portion of said polyoxyalkylene segment being bonded to said polydiorganosiloxane segment, any terminal portion of said polyoxyalkylene segment not bonded to said polydiorganosiloxane segment being satisfied by a terminating radical;

(d) optionally a second organic surfactant which is silicone-free;

wherein said surfactant component is present in an amount effective to form a stable emulsion of said oil phase in said water phase.

DETAILED DESCRIPTION OF THE INVENTION

The cosmetic compositions of the present invention are useful in a variety of makeup products such as foundations, eyeshadows, blushes, and the like. The invention permits incorporation of pigment into the oil phase of oil-in-water emulsions, resulting in fluid products with excellent blendino capability. In particular, the present invention avoids the problem known as "setting", in which the attempt to blend high amounts of pigment into the water phase leads to a product which cannot be applied in a satisfactory manner and results in an uneven, draggy, streaky appearance upon skin application. Thus, the present invention permits incorporation of higher amounts of pigment than previously thought possible in oil-in-water emulsion products.

The oil phase comprises 10 to 80 weight percent of the composition, preferably 10 to 50 weight percent thereof. It contains as the major component one or both of dimethyl polysiloxane having the chemical formula (1)

$$(CH_3)_3SiO(Si(CH_3)_2O)_d\text{-}Si(CH_3)_3 \qquad (1)$$

in which the degree of polymerization d has a value, typically between 1 and 4160, effective to give the fluid a viscosity of 0.65 to one million centistokes at 25° C.; and/or a cyclomethicone having D=3 to 6 repeating units of formula (2):

$$-(Si(CH_3)_2O)_D\text{-} \qquad (2)$$

The combined amount(s) of dimethyl polysiloxane, cyclomethicone, and organopolysiloxane of the formula $X(CH_3)_2SiO\text{-}Y\text{-}Si(CH_3)_2X$ preferably comprise about 10 to about 90 weight percent of the emulsion.

The hydrophobic coated pigments useful in the present invention have one of the following formulas:

$$P\text{-}[\text{-}O\text{-}Si\text{-}[\text{-}(OSiA_2)_{0\text{-}100}\text{-}A]_3]_{1\text{-}100} \qquad (3)$$

wherein each of the oxygen atoms at the left end of formula (3) is attached to an atom P in the pigment surface; and each A is an alkyl or alkenyl group having up to 30 carbon atoms. A number of adjacent polysiloxane chains as shown in formula (3) can be cross-linked through oxygen atoms to form a polysiloxane chain with up to 100 repeating-Si(-OP)-O-units that extends along the pigment surface, in addition to the polysiloxane chain which extends away from the pigment surface. Examples of alkyl groups are methyl, ethyl, propyl, butyl, pentyl, hexyl, heptyl, octyl, and so forth up to octadecyl. "Alkenyl" in cludes carbon chains with one or more double bonds; examples of such groups include ethylene, propylene, acrylyl, methacrylyl, and residues of unsaturated fatty acids such as oleic ($C_{17}H_{33}$-), linoleic ($C_{17}H_{31}$-), and linolenic ($C_{17}H_{29}$-).

The coated pigments can also exhibit structural formula (4):

$$P\text{-}O\text{-}(Si(CH_3)_2O)_p\text{—}Si(CH_3)_3 \qquad (4)$$

wherein p is 1–100, and P is an atom in the pigment surface.

The coated pigments can also exhibit structural formula (5):

$$(CH_3)_3SiO\text{-}[Si(CH_3)(\text{—}OP)\text{—}O\text{-}Si(CH_3)(\text{—}O\text{—}P\text{—})\text{—}O\text{—}]_{1\text{-}50}\text{—}Si(CH_3)_3 \quad (5)$$

wherein P is an atom in the pigment surface, and in which each of the up to 100 repeating (Si-O) units is bonded through an oxygen atom to the pigment surface.

The number of polysiloxane chains of formulas (3), (4), and (5) that are bonded to the pigment surface is not known but is sufficiently high to coat the pigment completely and render it completely hydrophobic. Hydrophobicity can readily be determined by placing the coated pigment into water and observing whether any becomes dispersed or suspended in the water.

Suitable pigments include all inorganic and organic pigments or fillers which are usable in cosmetic formulations. Particular examples include talc, mica, titanium dioxide, ferric oxide, ferrous oxide, kaolin, ultramarine, chromium oxide, chromium hydroxide, zinc oxide, silica, manganese violet, and their eguivalents. Other examples include lakes of organic colorants such as FD & C Red No. 7 calcium lake, FD & C Yellow No. 5 aluminum lake, D & C Red No. 9 barium lake, and D & C Red No. 30.

The pigment (or a mixture of two or more pigments) can be coated by placing it in dry, finely divided form in a mixer and adding a silicone material selected from the group consisting of (A) $A_1SiX_1X_2X_3$, wherein A is an alkyl or alkenyl group having 1 to 30 carbon atoms, and $X_1$, $X_2$ and $X_3$ are independently chloro, methoxy, or ethoxy (this material will form coated pigment having formula (3));

(B) material of the formula $$(CH_3)_3Si\text{—}(Si(CH_3)_2O)_p\text{—}Si(CH_3(_2OA_2$$

wherein p is 1 to 100, and $A_2$ is hydrogen or an alkyl group having 1 to 30 carbon atoms (this material will form coated pigment having formula (4));

(C) material of the formula $$(CH_3)_3SiO(Si(CH_3)(H)\text{—}O)_i\text{—}Si(CH_3)_3$$

wherein i is 1 to 100 (this material will form coated pigment having formula (5)); or a one-phase mixture of two or all three of A, B, and C. The relative amounts of fluid: pigment should be sufficient to coat the pigment particles. Generally a fluid: pigment weight ratio is satisfactory for which 1–4 weight percent of the final product is silicone. The pigment and fluid are intimately mixed thoroughly to obtain a uniform dispersion of the fluid on the pigment, in which the fluid completely coats the particles of pigment. The slurrying operation is advantageously carried out at a temperature of 25° C. to 160° C. effective to promote hydrolysis and reaction of the silicone with the pigment. As an alternative to synthesis, satisfactory coated pigments usable in this invention are commercially available from a variety of sources.

The coated pigment comprises about 2 to about 40 weight percent, and preferably about 5 to about 30 weight percent, of the emulsion.

The oil phase may also contain optional cosmetically acceptable oil-soluble components, such as preservatives, (e.g. up to 0.5 weight percent of the oil phase of paraben such as propyl paraben); up to 1 percent by weight of the oil phase of any conventional cosmetically acceptable fragrance; and one or more of other components well-known to cosmetic chemists, such as those that are intended for cosmetic purposes, for skin-softening and/or for physiological purposes, e.g. for treating skin conditions, like dry skin or chapped skin.

Examples of oil-soluble personal-care components that are useful in the compositions of this invention include, but are not limited to ester waxes, oils and fats of animal or vegetable origin, such as spermaceti wax; beeswax, carnauba wax, lanolin wax, coconut oil, castor oil and lanolin oil; fatty alcohols such as cetyl alcohol, stearyl alcohol and lauryl alcohol; fatty acids such as stearic acid and palmitic acid; alkyl esters of fatty acids such as the methyl, ethyl or isopropyl ester of said fatty acid; hydrocarbon oils and waxes such as mineral oil, petrolatum, perhydrosgualene and paraffin wax; and sunscreens such as octyldimethyl-PABA.

By "surfactant" is meant one or more than one surfactant compound as defined hereinbelow, provided that the compound or mixture of compounds used has the desired emulsion-stabilizing properties described herein. The surfactant must be capable of forming a stable oil-in-water emulsion, which means it will exhibit an HLB value of about 6 to about 18, preferably about 10 to about 14.

The surfactant includes one or more polydiorganisiloxaneoxyalkylene compounds. The polydiorganosiloxane segments of this surfactant consist of siloxane units which are interlinked by Si—O—Si linkages and which have the formula $$R_bSiO_{(4-b)/2}$$

The value of b may range from 0 to 3 for said siloxane units with the provision that there is an average of approximately 2, i.e. from 1.9 to 2.1 R radicals for every silicon atom in the copolymer. Suitable siloxane units thus include $R_3SiO_{1/2}$, $R_2SiO_{2/2}$, $RSiO_{3/2}$, and $SiO_{4/2}$ siloxane units taken is such molar amounts so that b has an average value of approximately 2 in the copolymer. Said siloxane units may be arranged in linear, cyclic and/or branched fashion.

The R radicals of this surfactant may be any radical selected from the group consisting of methyl, ethyl, vinyl, phenyl, and a divalent radical bonding a polyoxyalkylene segment to the polydiorganosiloxane segment. At least 95 percent of all R radicals are methyl radicals; preferablY there is at least one methyl radical bonded to each silicon atom. Divalent R radicals preferably contain no more than 6 carbon atoms. Examples of divalent R radicals include —O—, —$C_mH_{2m}O$—, —$CmH_{2m}$— and —$CmH_{2m}CO_2$— where m is an integer greater than zero.

Illustrative of the siloxane units that make up the polydiorganosiloxane segments of this first surfactant are the following, where Me denotes methyl and Q denotes said divalent R radical together with its bonded polyoxvalkylene segment: $R_3SiO_{1/2}$ units such as $Me_3SiO_{1/2}$, $Me_2(CH_2=CH)SiO_{1/2}$, $Me_2(C_6H_5)SiO_{1/2}$, $Me(C_6H_5))(CH_2=CH)SiO_{1/2}$, $Me_2(CH_3CH_2)SiO_{1/2}$, $Me_2QSiO_{1/2}$, $MeQ_2SiO_{1/2}$, $Q_3SiO_{1/2}$, $Q_2(CH_3CH_2)SiO_{1/2}$, and $Me(C_6H_5)(Q)SiO_{1/2}$; $R_2SiO_{2/2}$ units such as $Me_2SiO_{2/2}$, $Me(C_6H_5)SiO_{2/2}$, $Me(CH_2=CH)SiO_{2/2}$, $(C_6H_5)_2SiO_{2/2}$, $MeQSiO_{2/2}$, and $Q(C_6H_5)SiO_{2/2}$; $RSiO_{3/2}$, $CH_3CH_2SiO_{3/2}$ and $QSiO_{3/2}$; and $SiO_{4/2}$ units.

It is to be understood that the silicone-based surfactant may comprise one or more of said polydiorganosiloxane segments. The number of and average molecular weight of the polydiorganosiloxane segments in the copolymer is related to the desired weight ratio, hereinafter described, of the polysiloxane and polyoxyalkylene segments in the polymer. Preferably it comprises one polydiorganosiloxane segment having bonded thereto one or more polyoxyalkylene segments.

The polyoxyalkylene segments of this surfactant consist of oxyethylene units of the formula $-CH_2CH_2O-$, alone, or in combination with oxypropylene units of the formula $-CH_2CH(CH_3)O-$, an average of at least half of the oxyalkylene units in the polyoxyalkylene segments being oxyethylene units. Suitable emulsions of this invention are not formed when the polyoxyalkylene segments contain more than 50 mol percent of the relatively hydrophobic oxypropylene unit. The polyoxyalkylene segments thus correspond to the formula $(-CH(-CH_2CH_2O-)_p(-CH_2CH(CH_3)O-)_q$ wherein the oxyalkylene units may be arranged in any suitable fashion such as random, alternating and block. The average values of p and g are such that the value of p is egual to, or greater than, the value of g and the sum of $p+g$ is sufficient to provide an average molecular weight of under 5,000. Preferably, the value of p exceeds g.

The polyoxyalkylene segments are bonded to the polydiorganosiloxane segments by at least one terminal portion of said polyoxyalkylene segment, said bonding being by way of a divalent R radical, hereinbefore described. It is to be understood that said bonding may be by both terminal portions of said polyoxyalkylene segment in those copolymers comprising more than one polydiorganosiloxane segments. Any terminal portion of the polyoxyalkylene segment that is not bonded to a polydiorganosiloxane segment is satisfied by a terminating radical. The type of said terminating radical is not critical and may be monovalent, thereby terminating one polyoxyalkylene segment, or polyvalent, thereby terminating more than one polyoxyalkylene segment. Said terminating radicals are made up of atoms selected from the group consisting of carbon, hydrogen, nitrogen and oxygen. Illustrative of said terminating radicals are hydrogen; hydroxyl, alkyl, such as methyl, ethyl, propyl, butyl, benzyl, aryl, such as phenyl; alkoxy such as methoxy, ethoxy, propoxy, butoxy, benzyloxy; aryloxy, such as phenoxy; alkenyloxy, such as vinyloxy and allyloxy; acyloxy, such as phenoxy; alkenyloxy, such as vinyloxy and allyloxy; acyloxy, such as acetoxy, acryloxy and propionoxy and amino such as dimethylamino.

Herein "copolymer" means either a block arrangement of segments such as denoted by the formulae $(AB)_c$, $A(BA)_c$ and $B(AB)_c$ or a pendant arrangement of segments such as $(AB_d)_c$ or combinations thereof wherein A denotes a polydiorganosiloxane segment, B denotes a polyoxyalkylene segment and c and d denote integers greater than zero and greater than one, respectively. Copolymers (d) may be prepared by modification of the well-known methods described in the polydiorganosiloxane-polyoxyalkylene copolymer art. The following patents are hereby incorporated herein by reference to show the preparation of polydiorganosiloxane-polyoxyalkylene copolymers: Haluska, U.S. Pat. No. 2,868,824; Haluska, U.S. Pat. No. Re. 25,727; Bailey, U.S. Pat. No. 3,172,899; Pater, U.S. Pat. No. 3,234,252; Simmler, et al. U.S. Pat. No. 3,174,987; Bailey, et al., U.S. Pat. Nos. 3,562,786, 3,600,418 and 3,629,308; Holdstock, U.S. Pat. No. 3,629,165; and Gee et al., U.S. Pat. No. 4,122,029.

It is to be understood that the silicon-bonded reaction groups such as silicon-bonded hydrogen for addition reactions or silicon-bonded hydrolyzable radicals for displacement reactions are preferably completely reacted in the copolymer preparation process, but that trace amounts of said reaction groups may escape reaction with the polyoxyalkylene and may be found in the surfactant.

Non-essential components which are common to personal-care compositions of the art, such as perfumes, humectants, preservatives, colorants and electrolytes may be incorporated into the compositions of this invention provided they do not destablize the emulsion so as to cause a breaking or an inverting of the emulsion.

The cosmetic composition of the present invention can optionally further comprise a second surfactant which is organic, silicone-free, and has an HLB value provided that the overall effective HLB value of all surfactants present (preferably about 10 to about 14) still permits formation of the desired oil-in-water emulsion. The total amount of surfactant will typically be about 0.5 to 10 weight percent of the composition. As is well known to those of ordinary skill in this art, the HLB value is determined by a standardized technigue for measuring the solubility of a surfactant. The second surfactant may be anionic, cationic or non-ionic with respect to its hydrophilic portion.

Satisfactory second surfactants useful in this invention include "Tween 20" (HLB 16.7); "Arlacel 20" (HLB 8.7); and "Solulan 98" (HLB 13). Other examples of suitable surfactants include sodium capryl lactylate and sodium stearoyl lactylate as anionic surfactants, guatemary ammonium chlorides manufactured by Tomah Products, Inc. as Emulsifier Three TM and Emulsifier Four TM as cationic surfactants and polyethylene glycol (200) monolaurate, glycerol monolaurate, N,N-dimethylcaproamide, diethylene glycol monolaurate, sorbitan monolaurate and nonylphenoxy polyethoxyethanol as non-ionic surfactants. Other satisfactory silicone-free surfactants include the following: glyceryl monooleate, polyolyceryl-4 decaoleate, PEG-8 Oleate, PEG-4 lauryl ether, and PEG-9 lauryl ether. Other examples of suitable second surfactants having the proper HLB value may be found by reference to standard publications such as McCutcheon's, Detergents and Emulsifiers, Allred Publishing Company, Ridgewood, N.J. (1974).

The water phase of the composition of the present invention preferably comprises about 25 to about 80 weight percent of the emulsion. This phase may be simply water, or may contain water-soluble cosmetically acceptable components provided that the emulsion is not destabilized or inverted therein. Examples include ethanol; isopropanol; humectants, including glycerol, propylene glycol, sodium pyrrolidone carboxylic acids and citric acid, lactic acid and derivatives thereof; preservatives, such as methyl paraben; electrolytes, such as NaCl and magnesium sulfate; and sunscreens such as TEA-salicylate or PABA. The water phase comprises up to about 80 weight percent, preferably up to about 60 weight percent and more preferably up to about 50 weight percent, of the composition, and at least enought water to permit emulsification of the non-agueous components, preferably at least about 25 weight percent of the composition.

The composition can also contain effective amounts of optional cosmetically acceptable thickeners or other components such as cellulose derivatives, clays and organically modified clays, and organic thickeners to achieve desired properties such as viscosity, stability or afterfeel. Specific examples of such components are well-known to cosmetic chemists. Some examples are the following: sodium carboxymethyl cellulose, magnesium aluminum silicate, bentonite, hydroxyethyl cellulose, xanthan gum, cationic cellulosic resins, quaternium-18 hectorite, and glyceryl trihydroxy stearate. These modifiers can be added to the agueous or non-agueous phase of the composition.

To make the composition of the present invention, one simply (1) stirs thoroughly together all the components of the oil phase (the surfactant(s) are added to the phase (oil or water) in which they are more soluble), (2) disperses the hydrophobic pigments in the oil phase utilizing a high speed disperser or high shear mill and then (3) stirs the oil phase into the water phase including any components dissolved in the water phase. Any standard high speed stirring or homogenizing apparatus known to the art can be used to carry out the mixing operation. Preferably, components that are solid at room temperature (e.g. waxes), are heated to soften or liguify them prior to mixing with the other liguid components.

The invention will be described further in the following examples, which should be interpreted as illustrative rather than limiting. In each example, the indicated ingredients were combined into an "oil phase" mixture and a "water phase" mixture. The two mixtures were then thoroughly mixed together as described above, to produce a cosmetic product which was an oil-in-water emulsion having superior applicability, and non-dragging, non-streaking and non-setting properties.

EXAMPLE 1

| Component | Amount (% by weight) |
| --- | --- |
| Oil Phase | |
| Dimethicone (10 centistokes) | 15.0 |
| Cyclomethicone (D = 5) | 5.0 |
| Surfactant (Union Carbide "Silwet L7500" dimethicone copolyol, HLB = 10) | 1.0 |
| Pigment* | 15.0 |
| Aqueous Phase | |
| Water | 63.0 |
| Surfactant (Dow Corning 193 dimethicone copolyol, HLB = 13.6) | 1.0 |

*The pigment had been thoroughly coated with a polymethyl hydrogen siloxane coating bonded to the pigment surface.

EXAMPLE 2

| Components | Amount (% by weight) |
| --- | --- |
| Oil Phase | |
| Phenyl dimethicone (Dow Corning 556 fluid) | 15.0 |
| Dimethicone (viscosity 60 cs) | 8.0 |
| Surfactant (Silwet L7500, HLB = 10) | 1.5 |
| Pigment* | 20.0 |
| Water Phase | |
| Surfactant (Dow Corning 193, HLB = 13.6) | 1.2 |
| Xanthan gum | 0.5 |

| Components | Amount (% by weight) |
| --- | --- |
| Water | 53.8 |

*Pigment was coated with polymethyl hydrogen siloxane bonded to the pigment surface.

EXAMPLE 3

| Component | Amount (% by weight) |
| --- | --- |
| Oil Phase | |
| Phenyldimethicone | 15.0 |
| Cyclomethicone (D = 5) | 15.0 |
| Mineral oil (viscosity = 70 cs) | 5.0 |
| Surfactant (Silwet L7500, HLB = 10) | 1.0 |
| Pigment* | |
| Red and black iron oxides | 3.5 |
| Talc | 2.5 |
| TiO$_2$ | 10.0 |
| Sorbitan laurate (HLB = 8.7) | 0.5 |
| Water Phase | |
| Water | 40.0 |
| Magnesium aluminum silicate | 1.0 |
| Surfactant (Union Carbide Silwet L7001, HLB = 16) | 1.5 |
| Propylene Glycol | 5.0 |

*The pigment was coated with methyl trimethoxy silane to form a coating of polydimethyl siloxane bonded to the pigment surface.

EXAMPLE 4

| Component | Amount (% by weight) |
| --- | --- |
| Oil Phase | |
| Dimethicone (10 cs) | 10.0 |
| Cyclomethicone (D = 4) | 5.0 |
| Mineral oil | 10.0 |
| Pigment* | |
| Black, Yellow and Red Iron Oxides | 4.0 |
| TiO$_2$ | 16.0 |
| Talc | 5.0 |
| Water phase | |
| Surfactant (Dow Corning 193 fluid, HLB = 13.6) | 5.0 |
| Water | 39.5 |
| Ethanol | 5.0 |
| Xanthan gum | 0.5 |

*Pigment was coated with polymethylhydrogen siloxane bonded to the pigment surface and mineral oil.

EXAMPLE 5

| Component | Amount (% by weight) |
| --- | --- |
| Oil Phase | |
| Pigment* | |
| Iron Oxide | 8.00 |
| TiO$_2$ | 7.00 |
| Dimethicone (10 centistokes) | 12.00 |
| Cetyl alcohol | 2.0 |
| Stearyl dimethicone | 4.0 |
| Glycerol monolaurate | 0.50 |
| Bentonite | 2.0 |
| Preservative | 0.50 |
| Water Phase | |
| Water | 59.6 |
| Surfactant (Dimethicone copolyol, HLB = 13.6) | 5.0 |

*Pigment was coated as in Example 1.

EXAMPLE 6

| Component | Amount (% by weight) |
| --- | --- |
| Oil Phase | |
| Pigment* | |
| FD&C Red #7 | 5.00 |
| FD&C Yellow #5 | 5.00 |
| Iron Oxide | 10.00 |
| Talc | 10.00 |
| Surfactant (Silwet L7500, HLB = 10) | 3.00 |
| Surfactant (Silwet L722, HLB = 9) | 1.00 |
| Dimethicone (100 centistokes) | 10.00 |
| Cyclomethicone D = 5 | 15.00 |
| Glyerol tribehenate | 8.00 |
| Preservative | 0.50 |
| Water Phase | |
| Water | 30.50 |
| Surfactant (Dow Corning 193 dimethicone copolyol, HLB = 13.6) | 2.00 |

*Pigment was coated as in Example 1.

EXAMPLE 7

| Component | Amount (% by weight) |
| --- | --- |
| Oil Phase | |
| Surfactant (Silwet L7500, HLB = 10) | 2.50 |
| Pigment* | |
| Chromium Hydroxide Green | 10.00 |
| Ultramarine | 8.00 |
| titanated micas | 10.00 |
| Ceresin | 5.00 |
| Dimethicone (100 centistokes) | 10.00 |
| Cyclomethicone 80% D = 5, 20% D = 4 | 15.00 |
| Polymethyloctadecyl siloxane | 5.00 |
| Preservative | 0.50 |
| Water Phase | |
| Water | 31.50 |
| Surfactant (Dow Corning, 193 HLB = 13.6) | 2.5 |

*Pigment was coated as in Example 1.

What is claimed is:

1. A cosmetic composition which is an oil-in-water emulsion comprising:
  (a) About 10 to about 60 wt. % of the total weight of the composition of an oil phase which comprises
    (i) About 5 to about 30 wt. % of the emulsion of a coated pigment consisting essentially of finely divided particles of pigment whose surfaces are chemically bonded to, and physically completely coated by, polysiloxane which coating renders the particles hydrophobic, and
    (ii) a silicone component selected from the group consisting of dimethyl polysiloxane having the formula $(CH_3)_3SiO(Si(CH_3)_2O)_1-Si(CH_3)_3$ wherein the degree of polymerization d is effective to give the fluid a viscosity of 0.65 to one million centistokes at 25° C.; cyclomethicone having a degree of polymerization of 3 to 6; organopolysiloxane having the formula $X(CH_3)_2SiO-Y-Si(CH_3)_2X$ wherein X is alkyl or alkoxy having 1 to 30 carbon atoms and Y is a chain of 1 to 100 repeating (Si—O) units containing 1 to 100 units of the formula $(-Si(R_3)(R_4)O)$ wherein each of $R^1$, $R^2$, $R^3$ and $R^4$ can be alkyl containing 2 to 30 carbon atoms, phenyl, or phenyl connected to the Si atom by a vinyl group or an alkylene bridge 1 to 3 carbon atoms long; wherein each $R_1$ and $R_3$ can also be $-CH_3$, and each $R_1$ and $R_2$ can also be trimethylsiloxy; and mixtures thereof;
  (b) About 25 to about 60 wt. % of the total weight of the composition of an aqueous phase which comprises:
  (c) About 0.5 to about 10 wt. % of a surfactant component which comprises one or more polydiorganosiloxane-polyoxyalkylene copolymers containing at least one polydiorganosiloxane segment consisting of $R_bSiO_{(4-b)/2}$ siloxane units wherein b has a value of from 0 to 3 inclusive, there being an average of approximately two R radicals per silicon in the copolymer, and R denotes a radical selected from the group consisting of methyl, ethyl, vinyl, phenyl and a divalent radical bonding a polyoxyalkylene segment to the polydiorganosiloxane segment, at least 95 percent of all R radicals being methyl; and containing at least one polyoxyalkylene segment having an average molecular weight of less than 5000 and consisting of from 0 to 50 mol percent polyoxyalkylene units and from 50 to 100 mol percent polyoxyethylene units, at least one terminal portion of said polyoxyalkylene segment being bonded to said polydiorganosiloxane segment, any terminal portion of said polyoxyalkylene segment not bonded to said polydiorganosiloxane segment being satisfied by a terminating radical; and
    wherein said surfactant component is present in an amount effective to form a stable emulsion of said oil phase in said water phase.

2. A composition according to claim 1 wherein the pigment is one or more substances selected from the group consisting of talc, mica, titanium dioxide, ferric oxide, ferrous oxide, kaolin, ultramarine, chromium oxide, chromium hydroxide, zinc oxide, silica, manganese violet, and organic pigments.

3. A composition according to claim 1 further comprising a cosmetically acceptable component dissolved in the oil phase.

4. A composition according to claim 1 further comprising a cosmetically acceptable component dissolved in the aqueous phase.

5. A cosmetic composition which is an oil-in-water emulsion comprising
  (a) About 10 to about 50 wt. % of the total weight of the composition of an oil phase which comprises
    (i) About 5 to about 30 wt. % of the emulsion of a coated pigment consisting essentially of finely divided particles of pigment whose surfaces are chemically bonded to, and physically completely coated by, polysiloxane which coating renders the particles hydrophobic, and
    (ii) a silicone component selected from the group consisting of dimethyl polysiloxane having the formula $(CH_3)_3SiO(Si(CH_3)_2O)_d-Si(CH_3)_3$ wherein the degree of polymerization d is effective to give the fluid a viscosity of 0.65 to one million centistokes at 25° C.; cyclomethicone having a degree of polymerization of 3 to 6; organopolysiloxane having the formula $X(CH_3)_2SiO-Y-Si(CH_3)_2X$ wherein X is alkyl or alkoxy having 1 to 30 carbon atoms and Y is a chain of 1 to 100 repeating (Si—O) units containing 1 to 100 units of the formula (—Si($R_3$)($R_4$)O—) and 0 to 100 units of the formula (Si($R_3$)$R_4$)O) wherein each of $R^1$, $R^2$, $R^3$ and $R^4$ can be alkyl containing 2 to 30 carbon atoms, phenyl, or phenyl connected to the Si atom by a vinyl group or an alkylene bridge 1 to 3 carbon atoms long; wherein each $R^1$ and $R_3$ can also be —$CH_3$, and each $R^1$ and $R_2$ can also be trimethylsiloxy; and mixtures thereof;

(b) About 25 to about 60 wt. % of the total weight of the composition of an aqueous phase which comprises:

(c) About 0.5 to about 10 wt. % of a surfactant component which is a polydiorganosiloxane-polyoxyalkylene copolymer containing at least one polydiorganosiloxane segment consisting of

siloxane units wherein b has a value of from 0 to 3 inclusive, there being an average of approximately 2 R radicals per silicon in the copolymer, and R denotes a radical selected from the group consisting of methyl, ethyl, vinyl, phenyl and a divalent radical bonding a polyoxyalkylene segment to the polydiorganosiloxane segment, at least 95 percent of all R radicals being methyl; and containing at least one polyoxyalkylene segment having an average molecular weight of less than 5000 and consisting of from 0 to 50 mol percent polyoxyalkylene units and from 50 to 100 mol percent polyoxyethylene units, at least one terminal portion of said polyoxyalkylene segment being bonded to said polydiorganosiloxane segment, any terminal portion to said polyoxyalkylene segment not bonded to said polydiorganosiloxane segment being satisfied by a terminating radical;

(d) and further comprising 0.5 to 10 wt. % based on the total weight of the composition of a silicone-free surfactant;

wherein said surfactants are present in a combined amount effective to form a stable emulsion of said oil phase in said water phase.

6. A composition according to claim 5 wherein the pigment is one or more substances selected from the group consisting of talc, mica, titanium dioxide, ferric oxide, ferrous oxide, kaolin, ultramarine, chromium oxide, chromium hydroxide, zinc oxide, silica, manganese violet, and organic pigments.

7. A composition according ot claim 2 further comprising a cosmetically acceptable component dissolved in the oil phase.

8. A composition according to claim 2 further comprising a cosmetically acceptable component dissolved in the aqueous phase.

* * * * *